United States Patent
Kopreski et al.

(10) Patent No.: US 6,607,898 B1
(45) Date of Patent: *Aug. 19, 2003

(54) METHOD FOR DETECTION OF HTR AND HTERT TELOMERASE-ASSOCIATED RNA IN PLASMA OR SERUM

(75) Inventors: Michael S. Kopreski, Long Valley, NJ (US); Christopher D. Gocke, Elliott City, MD (US)

(73) Assignee: OncoMEDx, Inc., Long Valley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/653,573

(22) Filed: Aug. 31, 2000

Related U.S. Application Data

(63) Continuation-in-part of application No. 09/155,152, filed as application No. PCT/US97/03479 on Mar. 14, 1997, now Pat. No. 6,329,179.
(60) Provisional application No. 60/014,730, filed on Mar. 26, 1996.

(51) Int. Cl.$^7$ .............. C12P 19/34; C12Q 1/68; G01N 33/00; C07H 21/02; C07H 21/04
(52) U.S. Cl. .............. 435/91.2; 435/6; 435/91.1; 435/91.51; 436/94; 536/23.1; 536/24.3; 536/24.33
(58) Field of Search .............. 435/6, 91.1, 91.2, 435/91.51, 183; 436/94, 501; 536/23.1, 24.3, 24.33, 25.3

(56) References Cited

U.S. PATENT DOCUMENTS 5,576,178 A * 11/1996 Emanuel et al. .............. 435/6

FOREIGN PATENT DOCUMENTS

| DE | 198 04 372 A | | 9/1999 |
|----|---|---|---|
| EP | 0841 396 A | | 5/1998 |
| EP | 0 926 245 A | | 6/1999 |
| EP | 1 158 055 A | | 11/2001 |
| WO | WO 98 45450 A | | 10/1998 |
| WO | WO 99 40221 A | | 8/1999 |
| WO | WO-99/41426 | * | 8/1999 |
| WO | WO 00 46601 A | | 8/2000 |

OTHER PUBLICATIONS

Datta et al., Sensitive detection of occult breast cancer by the reverse–transcriptase polymerase chain reaction. Journal of Clinical Oncology, 12, 475–482, 1994.*
Feng et al., The RNA component human telomerase. Science, 1236–1241, Sep. 1, 1995.*
Keller et al., Fluorescence–based RT PCR analysis: Determination of the ratio of soluble to membrane–bound forms of FcrRIIA transcripts in hematopoietic cell lines. PCR Methods and Applications, 3, 32–38, 1993.*
Lay, Marla J. et al., Real–time fluorescence genotyping of factor V Leiden during rapid–cycle PCR, Clinical Chemistry 1997 pp. 2262–2267.*
Kopreski, Michael S. et al., Detection of Tumor Messenger RNA in the Serum of Patients with Malignant Melanoma, Aug. 1999, Clinical Cancer Research, vol. 5. pp. 1961–1965.*
Kyo et al., Expression of human telomerase subunits in ovarian malignant, borderline and benign tumors. Int. J. Cancer 80, 804–809, Mar. 1999.*
Wieczorek et al., Diagnostic and prognostic value of RNA–Proteolipid in sera of patients with malignant disorders following therapy: first clinical evaluation of a novel tumor marker. Cancer Res. 47, 6407–6412, 1987.*
Pfleiderer, Int. J. Cancer (Pred. Oncol.):64, 135–139 (1995).
Komeda, Cancer May 1995 1:75 (9):2214–9.
Boom et al., Journal of Clinical Microbiology, 28:495–503 (1990).
Meyerson et al., Cell. 90:785–795 (1997).
Nakamura et al., Science, 277:955–959 (1997).
Sommerfield et al., Cancer Research, 56:218–222 (1961).
Hiyama et al., Journal of the National Cancer Institute, 88:116–122 (1996).
Califano et al., Cancer Research 56:5720–5722 (1996).
Suehara et al., 3:2479–2483 (1997).

* cited by examiner

*Primary Examiner*—Ethan Whisenant
*Assistant Examiner*—Frank Lu
(74) *Attorney, Agent, or Firm*—McDonnell Boehnen Hulbert & Berghoff

(57) ABSTRACT

This invention relates to methods of detecting extracellular hTR RNA and hTERT RNA in blood, plasma, serum, and other bodily fluids. The invention thereby provides an aid for the detection, diagnosis, monitoring, treatment, or evaluation of neoplastic disease.

30 Claims, No Drawings

METHOD FOR DETECTION OF HTR AND HTERT TELOMERASE-ASSOCIATED RNA IN PLASMA OR SERUM

This application is a continuation-in-part of U.S. patent application, Ser. No. 09/155,152, filed Sep. 22, 1998, now U.S. Pat. No. 6,329,171 B1, the entire disclosure of which is hereby incorporated by reference, which is a 371 of PCT/US97/03479, filed Mar. 14, 1997, which claims the benefit of the filing date of Provisional U.S. patent application, Ser. No. 60/014,730, filed Mar. 26, 1996, the entire disclosure of which is hereby incorporated by reference.

BACKGROUND OF THE INVENTION

This invention relates to methods for detecting specific telomerase-associated RNA, those being telomerase RNA template (hTR) RNA and telomerase reverse transcriptase protein (hTERT) RNA, in bodily fluids including but not limited to plasma and serum.

Ribonucleic acid (RNA) is essential to the processes that allow translation of the genetic code to form proteins necessary for cellular functions, both in normal and neoplastic cells. While the genetic code structurally exists as deoxyribonucleic acid (DNA), it is the function of RNA to carry and translate this code to the cellular sites of protein production. The pathogenesis and regulation of cancer is dependent upon RNA-mediated translation of specific genetic codes to produce proteins involved with cell proliferation, regulation, and death, including but not limited to those RNA associated with specific cellular processes characteristic of cancer, such as processes associated with cellular longevity. Furthermore, some RNA and their translated proteins, although not necessarily involved in specific neoplastic pathogenesis or regulation, may serve to delineate recognizable characteristics of particular neoplasms by either being elevated or inappropriately expressed. The RNA associated with cancer and premalignant or neoplastic states have been referred to herein as tumor-derived, or tumor-associated RNA. The invention, as described in U.S. patent application Ser. No. 09/155,152, incorporated by reference herein in its entirety, provides a method by which tumor-associated or tumor-derived RNA in bodily fluids such as plasma and serum can be detected and thus utilized for the detection, monitoring, or evaluation of cancer or premalignant conditions. One group of tumor-associated or tumor-derived RNA are telomerase-associated RNA, comprising those RNA associated with the protein and nucleic acid components of telomerase.

Telomerase is a ribonucleoprotein ezyme which plays a role in stabilizing telomere length during cell replication. While most normal cells have low levels of telomerase activity, it has been shown that most cancer cells have high levels of telomerase activity (Hiyama, 1996; Sommerfeld, 1996). The telomerase ribonucleoprotein is thus a tumor-associated protein that can be considered a marker for cancer (Califano, 1996; Suehara, 1997). The telomerase ribonucleoprotein consists of components or subunits, two of these being telomerase RNA template (hTR), and telomerase reverse transcriptase protein (hTERT)(Meyerson, 1997; Nakamura, 1997).

U.S. patent application, Ser. No. 09/155,152, the entire disclosure of which is herein incorporated by reference, taught detection of telomerase-associated RNA in blood and other bodily fluids. The present invention describes a method of evaluating for two specific telomerase-associated RNA, hTR RNA and hTERT RNA, by detecting hTR MRNA or hTERT mRNA in blood, particularly plasma and serum, and other bodily fluids including but not limited to urine, effusions, ascites, saliva, cerebrospinal fluid, cervical, vaginal, and endometrial secretions, gastrointestinal secretions, bronchial secretions including sputum, and breast fluid.

SUMMARY OF THE INVENTION

The present invention provides a method for detecting hTR RNA and hTERT RNA in blood or a blood fraction, including plasma and serum, and other bodily fluids, the method comprising the steps of extracting RNA from blood, plasma, serum, and other bodily fluid, amplifying hTR RNA or hTERT RNA or their corresponding cDNA, and detecting the amplified product of hTR RNA or hTERT mRNA or their cDNA.

In a first aspect, the present invention provides methods for detecting hTR RNA and hTERT RNA in blood or blood fractions, including plasma and serum, in a human as an aid in the detection, diagnosis, monitoring, treatment, or evaluation of neoplastic disease, including early cancer, non-invasive cancer, carcinoma in-situ, premalignancy, invasive cancer, and advanced cancer, wherein the method comprises the steps of extracting RNA from blood or blood plasma or serum, amplifying a fraction of the extracted RNA or the corresponding cDNA wherein said fraction comprises hTR RNA or hTERT RNA, and detecting the amplified product of hTR RNA or hTERT RNA or their cDNA.

The invention further provides a method for detecting extracellular hTR RNA and hTERT RNA in all bodily fluids including but not limited to whole blood, plasma, serum, urine, effusions, ascitic fluid, saliva, cerebrospinal fluid, cervical secretions, vaginal secretions, endometrial secretions, gastrointestinal secretions, bronchial secretions including sputum, secretions or washings from the breast, and other associated tissue washings from a human as an aid in the detection, diagnosis, monitoring, treatment, or evaluation of neoplastic disease, including early cancer, non-invasive cancer, carcinoma in-situ, premalignancy, invasive cancer, and advanced cancer, wherein the method comprises the steps of extracting RNA from the bodily fluid, amplifying a fraction of the extracted RNA or the corresponding cDNA wherein the fraction comprises hTR RNA or hTERT RNA, and detecting the amplified product of hTR RNA or hTERT RNA or their cDNA.

The method of the invention further provides a method of inferring the presence of cells or tissue expressing hTR and/or hTERT in a human, wherein the method comprises the steps of extracting RNA from blood, plasma, serum or another bodily fluid, amplifying a fraction of the extracted RNA or the corresponding cDNA wherein said fraction comprises hTR RNA or hTERT RNA, and detecting the amplified product of hTR RNA or hTERT RNA or their cDNA, wherein detection infers the presence of cells or tissue in the human expressing hTR or hTERT.

The invention provides for primers useful in the amplification of hTR mRNA and hTERT mRNA and their corresponding cDNA.

The invention provides for a diagnostic kit enabling detection of hTR RNA or hTERT RNA from blood, plasma, serum, or other bodily fluids, in which primers or probes used in the amplification of hTR RNA or hTERT RNA or their corresponding cDNA are provided.

In preferred embodiments of the inventive methods, hTR RNA or hTERT RNA is extracted from blood, plasma, serum, or other bodily fluids using an extraction method selected from a group consisting of gelatin extraction method; silica, glass bead, or diatom extraction method; guanidinium thiocyanate acid-phenol based extraction methods; guanidinium thiocyanate acid based extraction methods; centrifugation through a cesium chloride or similar gradient; phenol-chloroform based extraction methods; or other commercially available RNA extraction methods.

In preferred embodiments of the inventive methods, hTR RNA or hTERT RNA or their corresponding cDNA is amplified using an amplification method selected from a group consisting of reverse transcriptase polymerase chain reaction; ligase chain reaction; DNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; and any combination or variation thereof.

In preferred embodiments of the inventive methods, detection of the amplified hTR RNA or hTERT RNA product or the corresponding cDNA product is performed using a detection method selected from a group consisting of gel electrophoresis; ELISA detection including modifications, including biotinylated or otherwise modified primers; hybridization using a specific, fluorescent-, radioisotope-, or chromogenically-labeled probe; Southern blot analysis; electrochemiluminescence; reverse dot blot detection; and high-performance liquid chromatography.

In a particularly preferred embodiment, hTR RNA or hTERT RNA is reverse transcribed to their corresponding cDNA prior to amplification.

The methods of the invention are provided as diagnostic methods for detecting extracellular hTR RNA or hTERT RNA in a human at risk for developing or who has developed a neoplastic, premalignant, or malignant disease consisting of cells expressing hTR or hTERT, wherein the methods comprise the steps of extracting RNA from bodily fluid, amplifying a fraction of the extracted RNA or the corresponding cDNA wherein said fraction comprises hTR RNA or hTERT RNA, and detecting the amplified product.

The methods of the invention thereby particularly provide diagnostic methods for identifying humans at risk for developing or who have malignancy or premalignancy, these malignancies including but not limited to breast, ovarian, lung, cervical, colorectal, gastric, pancreatic, bladder, endometrial, brain, kidney, and esophageal cancers, and these premalignancies and carcinoma in-situ including but not limited to cervical dysplasia, cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

The methods of the invention further provide a method to identify or select a human having hTR or hTERT expressing malignancy or premalignancy. The invention thereby provides a method to identify, stratify, or select a human who might benefit from a therapy, including but not limited to a telomerase-directed therapy, or from a further diagnostic test.

It is therefore the object of this invention to detect or infer the presence of hTR or hTERT expressing cancerous or precancerous cells within a human having a recognized cancer or pre-cancer, and in those not previously diagnosed, by examining the plasma or serum fraction of blood, or examining other bodily fluid, for extracellular hTR mRNA or hTERT mRNA in either a qualitative or quantitative fashion.

An advantageous application of this invention is to therefore allow identification of humans having malignancies and premalignancies.

Another advantageous application of this invention is to allow identification of humans having hTR or hTERT expressing neoplasms.

Another advantageous application of this invention is to allow selection of humans for therapies, including biotherapy, hormonal therapy, anti-sense therapies, chemotherapy, vaccines, anti-angiogenic therapy, radiation therapy, and surgery.

Another advantageous application of this invention is to provide a marker as a guide to whether adequate therapeutic effect has been achieved, or whether additional or more advanced therapy is required, and to assess prognosis in these patients.

Another advantageous application of this invention is to allow identification or analysis, either quantitatively or qualitatively, of hTR RNA or hTERT RNA in plasma or serum of humans during or following surgical procedures to remove premalignant or malignant lesions, and thus allow stratification of such patients as to their risk of residual cancer following the surgery, and their need for further therapy.

Another advantageous application of this invention is to allow identification or analysis of hTR RNA or hTERT RNA, either qualitatively or quantitatively, in the blood or other bodily fluid of a human who has completed therapy as an early indicator or relapsed cancer, impending relapse, or treatment failure.

Specific preferred embodiments of the present invention will become evident from the following more detailed description of certain preferred embodiments and the claims.

DETAILED DESCRIPTION OF THE INVENTION

The invention relates to methods of detecting extracellular hTR RNA and hTERT RNA in the blood or bodily fluid of a human, wherein the method consists of steps of first extracting RNA containing hTR RNA or hTERT RNA from blood or another bodily fluid; second, amplifying hTR RNA or hTERT RNA or the corresponding cDNA produced by reverse transcription; and third, detecting the amplified product of hTR RNA or hTERT RNA or their amplified cDNA product. The invention provides that hTR RNA and hTERT RNA may be detected independently, separately, or in combination with each other, and further that they may be detected in a sequential fashion, or in a multiplexed assay, or in a chip assay, and further, that they may be detected in combination with other tumor-derived or tumor-associated nucleic acid. hTR RNA or hTERT RNA may be extracted from a bodily fluid, including but not limited to whole blood, plasma, serum, urine, effusions, ascitic fluid, saliva, cerebrospinal fluid, cervical secretions, vaginal secretions, endometrial secretions, gastrointestinal secretions, bronchial secretions including sputum, and breast fluid or secretions, using the methods of extraction as detailed in U.S. patent application Ser. No. 09/155,152, the entire disclosure of which has hereby been incorporated by reference. In one preferred embodiment, hTR RNA or hTERT RNA is extracted from serum or plasma. It is preferred that blood be processed soon after drawing, and preferably within three hours, as to minimize any degradation of nucleic acids. In the preferred embodiment, blood is first collected by venipuncture and kept on ice and within 30 minutes of drawing the blood, serum is separated by centrifugation at 1100×g for 10 minutes at 4 degrees centigrade. Sera may then be frozen at −70 degrees centigrade until further assayed. RNA is extracted from the thawed serum following a rapid thawing such as in a water bath at 37 degrees centigrade, with extraction performed using a commercial kit such as but not limited to the Perfect RNA Total RNA Isolation Kit (Five Prime—Three Prime, Inc., Boulder, Colo.), performed according to the manufacturer's directions. Other methods of RNA extraction are further provided in U.S. patent application Ser. No. 09/155,152, incorporated herein by reference.

Following the extraction of RNA from the bodily fluid, a fraction of which contains hTR RNA and/or hTERT RNA, the hTR RNA or hTERT RNA is amplified. Applicable amplifications assays are detailed in U.S. patent application Ser. No. 09/155,152, as herein incorporated by reference, and include but are not limited to reverse transcriptase polymerase chain reaction (RT-PCR), ligase chain reaction, DNA signal amplification, amplifiable RNA reporters, Q-beta replication, transcription-based amplification, boomerang DNA amplification, strand displacement activation, cycling probe technology, isothermal nucleic acid sequence based amplification, and other self-sustained sequence replication assays.

In a preferred embodiment of the invention, hTR RNA or hTERT RNA is reverse transcribed to its corresponding cDNA prior to amplification using methods known in the art; wherein in one such method, reverse transcription for each sample is performed in a 30 microliter volume containing 200 units of MMLV reverse transcriptase (Promega, Madison, Wis.), 1×reaction buffer, 1 mM dNTPs, 0.5 micrograms random hexamers, 25 units of RNAsin (Promega, Madison, Wis.), and a fraction of previously extracted RNA such as 10 microliters of extracted serum RNA. The samples are then overlaid with mineral oil, and then incubated at room temperature for 10 minutes followed by 37 degrees centigrade for one hour.

In a preferred embodiment, one-third of the volume resulting from reverse transcription (10 microliters) is prepared for polymerase chain reaction amplification to amplify and detect cDNA of the hTERT subunit of telomerase. Primers for amplification are selected to be specific to the hTERT subunit. In a preferred embodiment, the preferred oligonucleotide primers are:

hTERT1 5'-CAGGAGCTGACGTGGAAGAT-3' (Seq ID NO:1)

hTERT2 5'-ACACACTCATCAGCCAGTGC-3' (Seq ID NO:2)

hTERT5 5'-TTGCAACTTGCTCCAGACAC-3' (Seq ID NO:3)

It is obvious to one skilled in the art that a number of other oligonucleot primer configurations might work equally well. This set has the advantage of spanning the second intron of the hTERT gene, thus preventing the amplification of any genomic DNA at the time of cDNA amplification. A PCR reaction is prepared using 10 microliters of the cDNA, 1 picomole each of primers hTERT1 and hTERT5, 1×Amplitaq Gold (PE Biosystems, Foster City, Calif.) reaction buffer, 1.5 mM $MgCl_2$, 200 micromolar dNTPs, 1 unit of Amplitaq Gold polymerase (PE Biosystems), and water to a final volume of 50 microliters. The cycling parameters were denaturation at 94 degrees centigrade for one minute, annealing at 55 degrees centigrade for one minute and extension at 72 degrees centigrade for one minute, repeated 25 cycles. A second round of amplification is then performed using the same constituents as above, except that 10 picomoles each of primers hTERT1 and hTERT2 are used to hemi-nest within the original pair and 5 microliters of the first round product substitutes for the cDNA. The cycling parameters are also similar except that 35 cycles are performed and the reaction concludes with an eight minute extension at 72 degrees centigrade.

In another preferred embodiment of the invention, one-third of the volume resulting from reverse transcription (10 microliters) is prepared for PCR amplification to detect cDNA of the hTR subunit of telomerase. Oligonucleotide primers specific to the hTR subunit are used, with the preferred primers being:

hTR1 5'-TCTAACCCTAACTGAGAAGGGCGTAG-3 ' (Seq ID NO:4)

hTR2 5'-GTTTGCTCTAGAATGAACGGTGGAAG-3 ' (Seq ID NO:5)

as described by Nakamura et al. (1997). It is obvious to one skilled in the art that a number of other oligonucleotide primer configurations might work equally well. A PCR reaction is prepared using 10 microliters of the cDNA, 10 picomoles each of primers hTR1 and hTR2, 1×Amplitaq Gold (PE Biosystems, Foster City, Calif.) reaction buffer, 1.5 mM $MgCl_2$, 200 micromolar dNTPs, 1 unit of Amplitaq Gold polymerase (PE Biosystems), and water to a final volume of 50 microliters. The cycling parameters were denaturation at 94 degrees centigrade for 45 seconds, annealing at 55 degrees centigrade for 45 seconds and extension at 72 degrees centigrade for ninety seconds, repeated 35 cycles and finishing with an eight minute extension at 72 degrees centigrade.

Following amplification, the hTR RNA or hTERT RNA or their corresponding cDNA amplified product is detected. In preferred embodiments of the inventive methods, detection of the amplified hTERT mRNA or hTR mRNA product is performed using a detection method selected from a group consisting of gel electrophoresis; ELISA detection including modifications, including biotinylated or otherwise modified primers; hybridization using a specific, fluorescent-, radioisotope-, or chromogenically-labeled probe; Southern blot analysis; electrochemiluminescence; reverse dot blot detection; and high-performance liquid chromatography.

In a particularly preferred embodiment, detection is by gel electrophoresis through a 4% TBE agarose gel, with staining of products with ethidium bromide for identification of the product. The amplified hTR cDNA product is 125 base pairs in size, while the amplified hTERT cDNA product is 240 base pairs if the single-round reaction is performed, and 139 base pairs if the hemi-nested reaction is performed.

The methods of the invention described above may also be utilized in the detection of hTR RNA and hTERT RNA in cells or tissues.

The methods of the invention described above may further be utilized in a quantitative manner to determine the amount of hTR RNA and hTERT MRNA present in the bodily fluid sample. In a preferred embodiment, the Taqman technology (PE Biosystems) is employed with the primers indicated above along with a dye-labeled internal primer such as (5'-AGGAGCCCAGGGGTTGGCTG-3') for hTERT or (5'-TCAGACAGCACTTGAAGAGG-3') for hTR RNA. Alternative methods of quantification, such as serial dilution of samples and endpoint PCR detection, are also envisioned within the invention. It is obvious to one skilled in the art that other oligonucleotide primers may be equally efficacious.

The methods of the invention as described above are similarly performed for the detection of extracellular hTR RNA and hTERT RNA from various bodily fluids, including but not limited to whole blood, urine, effusions, ascitic fluid, saliva, cerebrospinal fluid, cervical secretions, vaginal secretions, endometrial secretions, gastrointestinal secretions, breast fluid or secretions, and bronchial secretions including sputum. The invention as described thereby provides the method of amplifying and detecting extracellular hTR RNA and hTERT RNA.

The invention provides a diagnostic method for detecting hTR and hTERT mRNA in a human at risk for developing or who has developed a neoplastic, premalignant, or malignant disease consisting of cells expressing hTR or hTERT. The invention further provides a method of identifying humans at risk for developing, or who have cancers or premalignant disease, including but not limited to breast, ovarian, lung, cervical, colorectal, gastric, head and neck, pancreatic, bladder, endometrial, brain, kidney, and esophageal cancers, and premalignant disease and carcinoma in-situ including but not limited to cervical dysplasia and cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

The invention thereby provides a diagnostic method for detecting mRNA of telomerase components or related proteins in a human at risk for developing or who has developed a neoplastic, premalignant, or malignant disease.

The diagnostic methods and advantageous applications of the invention may further be provided through a diagnostic kit, wherein the kit includes primers or probes to the RNA of telomerase components or related proteins.

The inventive methods of amplification and detection of mRNA of telomerase components or related proteins in bodily fluids further provide significant utility in the assignment and monitoring of both non-specific therapies, and telomerase-specific therapies. The invention enables stratification and selection of patients likely to benefit from telomerase-specific therapy, and provides a method of monitoring response, relapse, and prognosis. Of particular value, the invention allows the development and application of telomerase-specific therapy even when only premalignant tumors, early cancer, or occult cancers or metastases such as following resection or in minimal residual disease are present. Thus, the invention allows therapeutic intervention when tumor burden is low, immunologic function is relatively intact, and the patient is not compromised, all increasing the potential for cure.

The methods of the invention and preferred uses for the methods of the invention are more fully illustrated in the following Example. This Example illustrates certain aspects of the above-described method and advantageous results. This Example is shown by way of illustration and not by way of limitation.

EXAMPLE 1

Sera were prepared from eighteen patients with small or resectable pancreatic cancers in the manner described above. Approximately 1.75 ML of serum from each patient was frozen at −80 degrees before using the invention detailed above. The sera were rapidly thawed and mRNA was prepared by the use of the Perfect RNA Total RNA Isolation Kit (Five Prime-Three Prime, Inc.). One-fifth of the total volume was reverse transcribed using MMLV reverse transcriptase (Promega, Madison, Wis.) as described in the inventive methods as above. PCR amplification of the resulting cDNA was then performed on 10 microliters (one-third volume) using either the hTR primers and conditions or the hemi-nested hTERT primers and conditions as separate reactions sequentially performed on all sera. Amplified hTR cDNA and hTERT cDNA product were detected by agarose gel electrophoresis. It was found that 9 of the 18 patients (50%) demonstrated hTERT RNA in their serum, and 7 of 18 (39%) demonstrated hTR RNA in their serum. Overall, 13 of 18 (72%) demonstrated either hTR or hTERT RNA in their serum. It was further demonstrated that the percentage of patients yielding positive results could be increased by testing sera for additional tumor-associated extracellular nucleic acids present in the sera, in this case extracellular mutant K-ras DNA. Positive and negative controls were appropriate for all reactions.

BIBLIOGRAPHY

1. Califano, J., Ahrendt, S. A., Meininger, G., Westra, W. H., Koch, W. M., and Sidransky, D.: Detection of telomerase activity in oral rinses from head and neck squamous cell carcinoma patients. Cancer Res., 56:5720–5722, 1996.
2. Hiyama, E., Gollahon, L., Kataoka, T., Kuroi, K., Yokoyama, T., Gazdar, A. F., Hiyama, K., Piatyszek, M. A., and Shay, J. W.: Telomerase activity in human breast tumors. J. Nat. Cancer Inst., 88: 116–122, 1996.
3. Meyerson, M., Counter, C. M., Eaton, E. N., Ellisen, L. W., Steiner, P., Caddle, S. D., Ziaugra, L., Beijersbergen, R. L., Davidoff, M. J., Liu, Q., Bacchetti, S., Haber, D. A., Weinberg, R. A.: hEST2, the putative human telomerase catalytic subunit gene, is up-regulated in tumor cells and during immortalization. Cell, 90: 785–795, 1997.
4. Nakamura, T. M., Morin, G. B., Chapman, K. B., Weinrich, S. L., Andrews, W. H., Lingner, J., Harley, C. B., and Cech, T. R.: Telomerase catalytic subunit homologs from fission yeast and human. Science, 277: 955–959, 1997.
5. Sommerfeld, H-J, Meeker, A. K., Piatyszek, M. A., Bova, G. S., Shay, J. W., and Coffey, D. S.: Telomerase activity: A prevalent marker of malignant human prostate tissue. Cancer Res. 56: 218–222, 1996.
6. Suehara, N., Mizumoto, K., Tanaka, M., Niiyama, H., Yokohata, K., Tominaga, Y., Shimura, H., Muta, T., and Hamasaki, N.: Telomerase activity in pancreatic juice differentiates ductal carcinoma from adenoma and pancreatitis. Clin. Cancer Res., 3: 2479–2483, 1997.

What is claimed is:

1. A method for detecting extracellular human telomerase RNA template (hTR) RNA in blood plasma or serum for detecting, diagnosing, monitoring, treating or evaluating neoplastic disease comprising cells that express hTR, the method comprising the steps of:

a) extracting mammalian, heterogeneous extracellular RNA from human blood plasma or serum;

b) amplifying a portion of the extracted extracellular RNA or cDNA produced therefrom wherein said portion comprises hTR RNA to produce an amplified product, and wherein amplification is performed qualitatively or quantitatively using primers or probes that target hTR RNA or the corresponding cDNA; and c) detecting qualitatively or quantitatively the amplified product produced from hTR RNA or corresponding cDNA.

2. The method of claim 1, wherein the amplification in step b) is performed by an amplification method that is reverse transcriptase polymerase chain reaction, ligase chain reaction, branched DNA signal amplification, amplifiable RNA reporters, Q-beta replication, transcription-based amplification, isothermal nucleic acid sequence based amplification, self-sustained sequence replication assays, boomerang DNA amplification, strand displacement activation, or cycling probe technology, wherein the RNA is first reverse-transcribed into a corresponding cDNA in said methods requiring said conversion.

3. The method of claim 1, wherein the amplified product in step c) is detected by gel electrophoresis, capillary electrophoresis, ELISA detection using biotinylated or modified primers, labeled fluorescent or chromogenic probe, Southern blot analysis, Northern blot analysis, electrochemiluminescence, laser-induced fluorescence, reverse dot blot detection, or high-performance liquid chromatography.

4. A method according to claim 1, wherein a human at risk for a malignancy or premalignancy is screened for malignancy or premalignancy, wherein said malignancy or premalignancy is associated with human telomerase template RNA (hTR), and wherein detection of hTR RNA in the plasma or serum fraction of blood of said human indicates that malignant or premalignant cells are present in the body of said human.

5. A method according to claim 1, wherein the human is a human at risk for a malignancy or premalignancy and detection of the amplified product is used to screen the human for.malignancy or premalignancy, wherein said malignancy or premalignancy is associated with expression of human telomerase RNA template (hTR) RNA, and wherein detection of hTR RNA or in blood plasma or serum of said human indicates that malignant or premalignant cells are present in the body of said human.

6. The method of claim 5, wherein the malignancy or premalignancy is a malignancy of breast, head and neck, ovarian, lung, cervical, colorectal, gastric, liver, prostate, pancreatic, bladder, endometrial, brain, kidney, or esophageal tissue, or a melanoma or sarcoma, or a premalignancy that is cervical dysplasia, cervical intraepithelial neoplasia, bronchial dysplasia, atypical hyperplasia of the breast, ductal carcinoma in-situ, colorectal adenoma, atypical endometrial hyperplasia, or Barrett's esophagus.

7. A method for selecting a human with a cancer for a cancer therapy, the method comprising the steps of detecting human telomerase RNA in blood plasma or serum in said human using the method of claim 1 and selecting a human with cancer having hTR in said blood plasma or serum for the cancer therapy.

8. A method of determining a need for a diagnostic test in a human for malignancy or premalignancy, the method comprising the steps of detecting human telomerase RNA in blood plasma or serum in said human using the method of claim 1 and determining a need for a diagnostic test in said human for malignancy or premalignancy based on the presence or absence of hTR in said blood plasma or serum in said human.

9. A method for monitoring a therapy administered to a human, the method comprising the steps of monitoring said therapy by detecting an amount or level of human telomerase RNA in blood plasma or serum in said human using the method of claim 1.

10. The method of claim 1, wherein quantitative amplification is performed using a dye-labeled primer or probe.

11. A method according to claim 1, wherein the method comprises the additional step of quantitatively or qualitatively comparing the product of human telomerase RNA template (hTR) RNA in the plasma or serum of a human subject to the product of hTR RNA in the plasma or serum from a plurality of humans with or without known malignancy or premalignancy.

12. A method of detecting extracellular human telomerase RNA template (hTR) RNA in a bodily fluid for detecting, diagnosing, monitoring, treating or evaluating neoplastic disease comprising cells that express hTR, the method comprising the steps of:
  a) extracting mammalian, heterogeneous extracellular RNA from a human bodily fluid;
  b) amplifying a portion of the extracted, extracellular RNA or cDNA produced therefrom wherein said portion comprises hTR RNA to produce an amplified product, and wherein amplification is performed qualitatively or quantitatively using primers or probes that target hTR RNA or the corresponding cDNA; and
  c) detecting qualitatively or quantitatively the amplified product produced from hTR RNA or corresponding cDNA.

13. The method of claim 12, wherein the amplification in step b) is performed by an amplification method that is reverse transcriptase polymerase chain reaction, ligase chain reaction, branched DNA signal amplification, amplifiable RNA reporters, Q-beta replication, transcription-based amplification, isothermal nucleic acid sequence based amplification, self-sustained sequence replication assays, boomerang DNA amplification, strand displacement activation, or cycling probe technology, wherein the RNA is first reverse-transcribed into a corresponding cDNA in said methods requiring said conversion.

14. The method of claim 12, wherein the amplified product in step c) is detected by gel electrophoresis, capillary electrophoresis, ELISA detection using biotinylated or modified primers, labeled fluorescent or chromogenic probe, Southern blot analysis, Northern blot analysis, electrochemiluminescence, laser-induced fluorescence, reverse dot blot detection, or high-performance liquid chromatography.

15. A method according to claim 12, wherein the human is a human at risk for a malignancy or premalignancy and detection of the amplified product is used to screen the human for malignancy or premalignancy, wherein said malignancy or premalignancy is associated with expression of human telomerase RNA template (hTR) RNA, and wherein detection of hTR RNA in an acellular fraction of a bodily fluid of said human indicates that malignant or premalignant cells are present in the body of said human.

16. The method of claim 15, wherein the malignancy or premalignancy is a malignancy of breast, head and neck, ovarian, lung, cervical, colorectal, gastric, liver, prostate, pancreatic, bladder, endometrial, brain, kidney, or esophageal tissue, or a melanoma or sarcoma, or a premalignancy that is cervical dysplasia, cervical intraepithelial neoplasia, bronchial dysplasia, atypical hyperplasia of the breast, ductal carcinoma in-situ, colorectal adenoma, atypical endometrial hyperplasia, or Barrett's esophagus.

17. A method for selecting a human with a cancer for a cancer therapy, the method comprising the steps of detecting human telomerase RNA in an acellular fraction of a hTR in said acellular fraction of said bodily fluid for the cancer therapy.

18. A method of determining a need for a diagnostic test in a human for malignancy or premalignancy, the method comprising the steps of detecting human telomerase RNA in an acellular fraction of a bodily fluid in said human using the method of claim 2 and determining a need for a diagnostic test in said human for malignancy or premalignancy based on the presence and absence of hTR in said acellular fraction of said bodily fluid in said human.

19. A method for monitoring a therapy administered to a human, the method comprising the steps of monitoring said therapy by detecting an amount or level of human telomerase RNA an acellular fraction of a bodily fluid in said human using the method of claim 2.

20. A method according to claim 12, wherein the bodily fluid is blood, urine, effusions, ascitic fluid, saliva, cerebrospinal fluid, cervical secretions, vaginal secretions, endometrial secretions, gastrointestinal secretions, bronchial secretions, sputum, or secretions or washings from the breast.

21. The method of claim 12, wherein quantitative amplification is performed using a dye-labeled primer or probe.

22. A method according to claim 12, wherein the method comprises the additional step of quantitatively or qualitatively comparing the product human telomerase RNA template (hTR) RNA in the bodily fluid of a human to the product of hTR RNA in the bodily fluid from a plurality of humans with or without known malignancy or premalignancy.

23. A method of identifying a human having human telomerase RNA template (hTR) expressing cells or tissue, the method comprising the steps of:
   a) extracting mammalian, heterogeneous extracellular RNA from blood plasma or serum from the human;
   b) amplifying a portion of the extracted extracellular RNA or cDNA produced therefrom wherein said portion comprises extracellular hTR RNA to produce an amplified product, and wherein amplification is performed qualitatively or quantitatively using primers or probes that target hTR RNA or the corresponding cDNA; and
   c) detecting the amplified product produced from hTR RNA or corresponding cDNA.

24. The method of claim 23, wherein the human telomerase RNA template (hTR) expressing cells or tissue comprises a malignancy, or premalignancy or carcinoma in-situ.

25. The method of claim 24, wherein the malignancy is a cancer of breast, ovarian, head and neck, lung, cervical, colorectal, gastric, liver, pancreatic, bladder, prostate, endometrial, brain, kidney, or esophageal tissue, or a melanoma or sarcoma.

26. The method of claim 24, wherein the premalignancy or carcinoma in-situ is cervical dysplasia, cervical intraepithelial neoplasia, bronchial dysplasia, atypical hyperplasia of the breast, ductal carcinoma in-situ, colorectal adenoma, atypical endometrial hyperplasia, or Barrett's esophagus.

27. The method of claim 23, wherein the human is one at risk for developing a malignancy or premalignancy.

28. A method of selecting a human with cancer for a cancer therapy, the method comprises the steps of:
   a) extracting mammalian, heterogeneous extracellular RNA from the human's blood plasma or serum;
   b) amplifying a portion of the extracted extracellular RNA or cDNA produced therefrom wherein said portion comprises human telomerase RNA template (hTR) RNA to produce an amplified product, and wherein amplification is performed qualitatively or quantitatively using primers or probes that target hTR RNA or the corresponding cDNA;
   c) detecting the amplified product produced from hTR RNA or corresponding cDNA, and
   d) selecting the human with cancer for the cancer therapy when the amplified product is detected.

29. A method for detecting human telomerase RNA template (hTR), or cDNA reverse-transcribed therefrom, comprising the steps of extracting RNA comprising human telomerase RNA template (hTR) RNA from blood plasma or serum, with or without converting said RNA to cDNA, hybridizing said RNA or cDNA to a detectably-labeled probe specific for hTR RNA or cDNA, and detecting hybridization of hTR RNA or cDNA with the detectably-labeled probe.

30. A method for detecting human telomerase RNA template (hTR) RNA, or cDNA reverse-transcribed therefrom, comprising the steps of extracting RNA comprising hTR RNA from an acellular fraction of a bodily fluid, with or without converting said RNA to cDNA, hybridizing said RNA or cDNA to a detectably-labeled probe specific for hTR RNA or cDNA, and detecting hybridization of hTR RNA or cDNA with the detectably-labeled probe.

* * * * *

```
SEQUENCE LISTING

<160> NUMBER OF SEQ ID NOS: 7

<210> SEQ ID NO 1
<211> LENGTH: 20
<212> TYPE: DNA
<213> ORGANISM: Homo sapiens

<400> SEQUENCE: 1
caggagctga cgtggaagat                                          20
```

```
<210> SEQ ID NO 2
<211> LENGTH: 20
<212> TYPE: DNA
<213> ORGANISM: Homo sapiens

<400> SEQUENCE: 2
acacactcat cagccagtgc                                                  20

<210> SEQ ID NO 3
<211> LENGTH: 20
<212> TYPE: DNA
<213> ORGANISM: Homo sapiens

<400> SEQUENCE: 3
ttgcaacttg ctccagacac                                                  20

<210> SEQ ID NO 4
<211> LENGTH: 26
<212> TYPE: DNA
<213> ORGANISM: Homo sapiens

<400> SEQUENCE: 4
tctaacccta actgagaagg gcgtag                                           26

<210> SEQ ID NO 5
<211> LENGTH: 26
<212> TYPE: DNA
<213> ORGANISM: Homo sapiens

<400> SEQUENCE: 5
gtttgctcta gaatgaacgg tggaag                                           26

<210> SEQ ID NO 6
<211> LENGTH: 20
<212> TYPE: DNA
<213> ORGANISM: Homo sapiens

<400> SEQUENCE: 6
aggagcccag gggttggctg                                                  20

<210> SEQ ID NO 7
<211> LENGTH: 20
<212> TYPE: DNA
<213> ORGANISM: Homo sapiens

<400> SEQUENCE: 7
tcagacagca cttgaagagg                                                  20
```